US00PP26029P3

(12) United States Plant Patent
Olesen

(10) Patent No.: US PP26,029 P3
(45) Date of Patent: Nov. 3, 2015

(54) MINIATURE ROSE PLANT NAMED 'POULTY014'

(50) Latin Name: ***Rosa* hybrid**
Varietal Denomination: Poulty014

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 182 days.

(21) Appl. No.: 13/986,941

(22) Filed: Jun. 14, 2013

(65) Prior Publication Data

US 2014/0373209 P1 Dec. 18, 2014

(51) Int. Cl.
*A01H 5/02* (2006.01)

(52) U.S. Cl.
USPC ..... Plt./118

(58) Field of Classification Search
USPC ..... Plt./101, 116, 118
See application file for complete search history.

(56) References Cited

PUBLICATIONS

Poulsen Roser A/S catalog; Retrieved from the Internet http://www.poulsenroser.com (1 page total).*
'HelpMeFind' website; Retrieved from the Internet http://www.helpmefind.com (1 page total).*
UPOV-Pluto Plant Variety Database International Union for the Protection of New Varieties of Plants, Jan. 19, 2015, obtained for cultivar name 'Poulty014' (1 page total).*
Poulsen Roser A/S catalog; Retrieved from the Internet http://www.poulsenroser.com on Jan. 29, 2015 (1 page total).*
'HelpMeFind' website; Retrieved from the Internet http://www.helpmefind.com Jan. 29, 2015 (1 page total).*

* cited by examiner

*Primary Examiner* — Susan McCormick Ewoldt

(57) ABSTRACT

A new miniature rose plant that has abundant, yellow flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty014'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulty014', originated as a single seedling from the stated cross.

The new variety may be distinguished from its male pollen parent and female seed parent primarily by flower coloration and growth habit. The female seed parent is 25 to 30 cm in height, while the claimed plant is 15 to 20 cm in height. The male pollen parent has apricot colored flowers, while the claimed rose variety has yellow flowers.

The objective of the hybridization of this rose variety for commercial culture was to create a new and distinct variety with unique qualities, such as:

1. Uniform and abundant yellow flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type, known to the inventor, and distinguish 'Poulty014' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty014' was selected by the inventor as a single plant from the progeny of the hybridization in 2007.

Asexual reproduction of 'Poulty014' by cuttings was first done by Mogens N. Olesen in the nursery in Fredensborg, Denmark in 2008. This initial and other subsequent propagations conducted in controlled environments have demonstrated that the characteristics of 'Poulty014' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty014'. Specifically illustrated in the drawing are flowers at various stages of development, flower in parts, leaves, and stems. Illustrated plants are 10 months of age.

DETAILED DESCRIPTION OF THE VARIETY

The following is a description of 'Poulty014', as observed in its growth in a field nursery in Benton County Oregon. Observed plants are 10 months of age. Color references are made using The Royal Horticultural Society (London, England) Colour Chart, 2001, except where common terms of color are used.

For a comparison, several physical characteristics of the rose variety 'Poulmist', U.S. Plant Pat. No. 18,975 are compared to 'Poulty014' in Chart 1.

CHART 1

| | 'Poulty014' | 'Poulmist' |
|---|---|---|
| Petalage: | 35 to 40 petals | 35 to 40 petals |
| Flower Diameter: | 45 mm | 40 mm |
| General Tonality of Flower Color: | Yellow Group 8A with intonations of Yellow Group 12A | Yellow Group 12B |

FLOWER AND FLOWER BUD

Blooming habit: Continuous.

Flower bud:

*Size.*—Upon opening, 17 mm in length from base of receptacle to end of bud. 11 mm in diameter.

*Bud form.*—Urceolate.

*Bud color.*—As sepals unfold, petals are Yellow Group 8C to 8A, with intonation of Orange-Red Group N34A and N34C.

*Sepals.*—Upper Surface: Color: Yellow-Green Group 144C. Texture: Smooth, moderately pubescent. Lower Surface: Color: Yellow Green Group 144A with intonations of Greyed-Red 182A. Texture: Smooth. Shape: Apex: Cirrhose. Base: Flat at union with receptacle. Margins: Margins have weak foliaceous appendages on three of the five sepals. Size: 10 mm long by 3 mm wide.

*Receptacle.*—Surface Texture: Smooth. Shape: Funnel shaped. Size: 3 mm tall and 6 mm wide. Color: Yellow Green Group 144A with intonations of Greyed-Orange Group 175A.

*Pedicel.*—Surface: Smooth. Length: 15 to 20 mm. Diameter: Generally 2 mm. Color: Yellow-Green Group 144A with intonations of Greyed-Orange Group 175A. Strength: Medium strength.

*Borne.*—Singly, or in clusters of 5 flower buds per flowering branch.

Flower bloom:

*Fragrance.*—None.

*Duration.*—As a pot plant, flowers last up to 28 days.

*Size.*—Flower diameter is 45 mm when open. Flower depth is 15 mm.

*Form.*—General shape is cupped with a flat upper portion and a convex lower portion.

Petalage: Under normal conditions, flowers have 35 to 40 petals total, 3 to 5 of which are petaloids.

Color:

*General tonality.*—On open flower Yellow Group 8A with intonations of Yellow Group 12 A.

*Upon opening, petals.*—Outermost and innermost petals are Yellow Group 9A on the upper surface. Yellow Group 8A with intonations of Yellow-Green Group 13A on the lower surface.

*After opening, petals.*—Outermost and innermost petals are Yellow Group 9B on the upper surface. Yellow-Green Group 8A on the lower surface.

Petals:

*Petal reflex.*—None.

*Margin.*—Entire, no undulations.

*Shape.*—Generally broad and elliptic. Apex shape: Rounded. Base shape: Acute.

*Size.*—15 mm (l) by 16 mm (w).

*Texture.*—Smooth.

*Thickness.*—Thin.

Petaloids:

*Quantity.*—3 to 5 on average.

*Shape.*—Irregular, and asymmetric. The apex and base are acute.

*Color.*—Yellow Group 9A on the upper surface. Yellow Group 8A with intonations of Yellow-Green Group 13A on the lower surface.

*Size.*—3 mm (l) by 3 mm (w).

Reproductive organs:

*Pollen.*—None Observed.

*Anthers.*—Size: 2 mm long. Color: Yellow Group 12B. Quantity: 25 on average.

*Filaments.*—Color: Yellow Group 13B. Length: About 2 mm.

*Pistils.*—Length: About 4 mm long. Quantity: 19 on average.

*Stigmas.*—Color: Greyed-Yellow Group 160C.

*Styles.*—Color: Green-White Group 157A.

*Seed formation.*—Not observed.

PLANT

Plant growth: Upright and bushy. Plants are 15 to 20 cm in height, and 15 cm wide.

Stems:

*Color.*—Juvenile growth: Yellow-Green Group 144A with Greyed-Orange Group 176A. Mature growth: Yellow-Green Group 146B.

*Length.*—Canes are 13 to 15 cm from the base of the plant to the flowering portion.

*Diameter.*—4 mm.

*Internodes.*—On mature canes, there is an average distance of 5 mm between nodes.

*Surface texture.*—Young and mature wood is smooth.

Prickles: None observed.

Plant foliage:

*Compound leaf size.*—90 mm (l) by 60 mm (w).

*Quantity.*—8 to 10 leaves per 10 cm of stem.

*Color of juvenile foliage.*—Upper side: Yellow-Green Group 146A. Lower side: Yellow-Green Group 146A.

*Color of mature foliage.*—Upper side: Yellow-Green Group 147A. Lower side: Yellow-Green Group 147B.

Plant leaves and leaflets:

*Stipules.*—Size: About 15 mm in length. Shape: Linear, slightly broad based with outward extending apecies. Margins: Finely serrated with few stipitate glands. Color: Yellow-Green Group 144A.

*Petiole.*—Length: 22 mm on average. Diameter: About 2 mm. Upper surface: Yellow-Green Group 144A. Lower surface: Yellow-Green Group 144B.

*Rachis.*—Length: 30 mm on average. Diameter: About 2 mm. Upper surface: Yellow-Green Group 144A. Lower surface: Yellow-Green Group 144B.

*Leaflet*.—Number of leaflets: 5 on normal leaves in middle of the stem. Size: 31 mm in length by 21 mm wide. Margin: Serrate. General Shape: Elliptical. Apex Shape: Acute to mucronate. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the miniature class named 'Poulty014', substantially as illustrated and described herein, due to its abundant, yellow flowers, vigorous growth, compact habit, suitability for production from softwood cuttings in pots, and durable flowers and foliage that make the variety suitable for distribution in the floral industry.

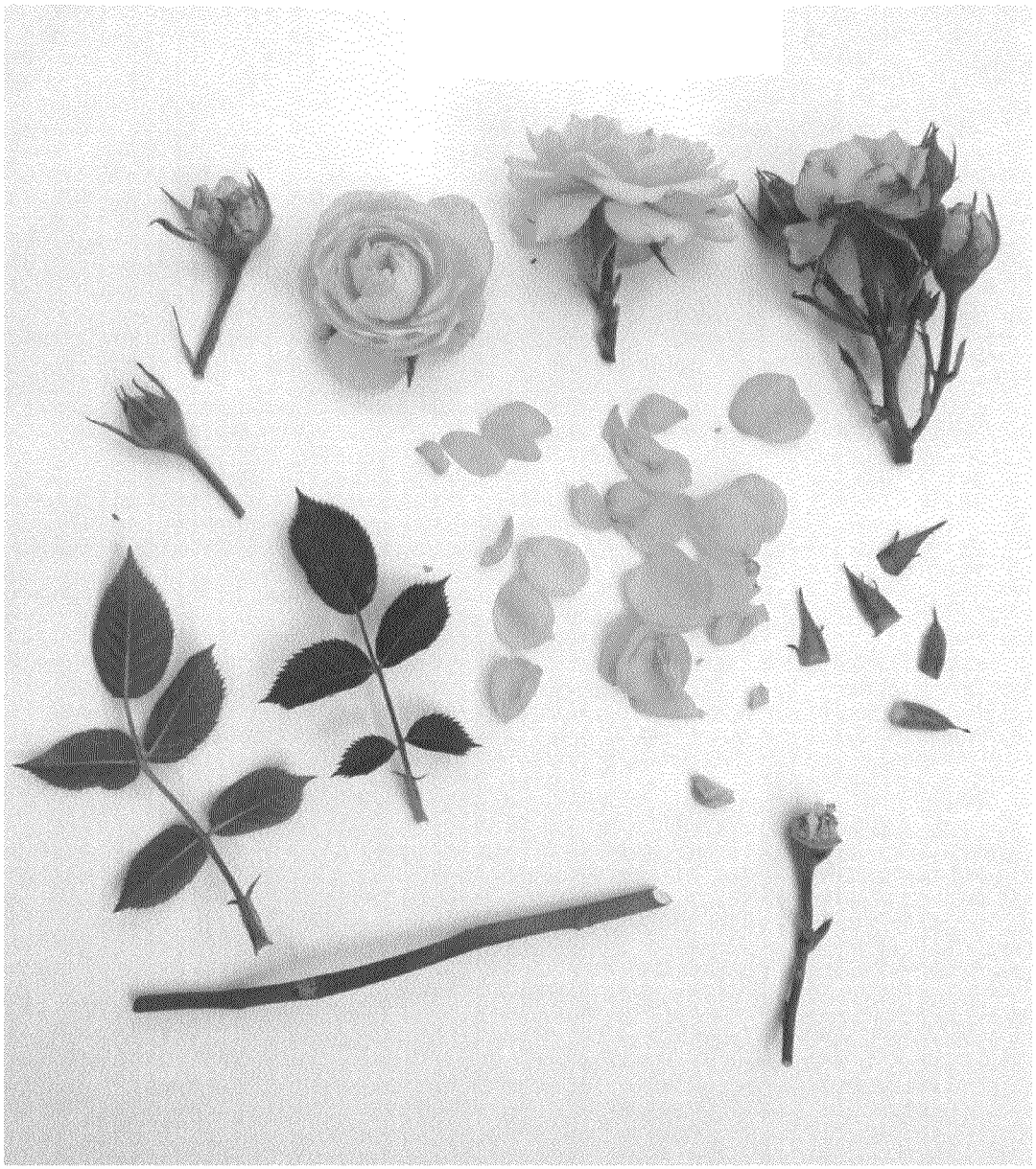

* * * * *